(12) United States Patent
Bosanac et al.

(10) Patent No.: US 12,125,582 B2
(45) Date of Patent: Oct. 22, 2024

(54) PREDICTING USER BODY VOLUME TO MANAGE MEDICAL TREATMENT AND MEDICATION

(71) Applicant: Advanced Health Intelligence, Ltd., South Perth (AU)

(72) Inventors: Vlado Bosanac, South Perth (AU); Amar El-Sallam, South Perth (AU)

(73) Assignee: Advanced Health Intelligence, Ltd., South Perth (AU)

( * ) Notice: Subject to any disclaimer, the term of this patent is extended or adjusted under 35 U.S.C. 154(b) by 355 days.

(21) Appl. No.: 17/658,077

(22) Filed: Apr. 5, 2022

(65) Prior Publication Data

US 2022/0319676 A1 Oct. 6, 2022

Related U.S. Application Data

(60) Provisional application No. 63/170,910, filed on Apr. 5, 2021.

(51) Int. Cl.
*G16H 30/40* (2018.01)
*G06F 18/214* (2023.01)
(Continued)

(52) U.S. Cl.
CPC ........... *G16H 30/40* (2018.01); *G06F 18/214* (2023.01); *G06N 20/00* (2019.01); *G16H 20/10* (2018.01); *G16H 70/40* (2018.01)

(58) Field of Classification Search
CPC ........ G16H 30/40; G16H 20/10; G16H 70/40; G16H 50/30; G16H 50/20; G06F 18/214;
(Continued)

(56) References Cited

U.S. PATENT DOCUMENTS 10,321,728 B1 6/2019 Koh et al.
2009/0099457 A1* 4/2009 Barnes ................... G16H 50/30
600/587

(Continued)

FOREIGN PATENT DOCUMENTS

CN 109685048 A 4/2019
EP 3742397 A1 11/2020
(Continued)

OTHER PUBLICATIONS

International Search Report and Written Opinion mailed Jun. 30, 2022 received in International Application No. PCT/IB2022/000191.

*Primary Examiner* — Juan A Torres
(74) *Attorney, Agent, or Firm* — Dorsey & Whitney LLP

(57) ABSTRACT

In some examples, an apparatus, such as a mobile phone may include a camera, a processor, and computer readable medium. The camera capture one or more images of a person. The processor may use a machine learning model to predict the body volume of the person based on the captured images. The model may be trained based at a training data set comprising at least a plurality of user images. The apparatus may transmit the predicted body volume to a medication and medical treatment management system and receive from the same an adjusted medication or medical treatment plan. The apparatus may further execute the adjusted medication or medical treatment plan.

23 Claims, 9 Drawing Sheets

(51) Int. Cl.
*G06N 20/00* (2019.01)
*G16H 20/10* (2018.01)
*G16H 70/40* (2018.01)

(58) Field of Classification Search
CPC ........ G06N 20/00; G06N 3/0464; G06N 3/08; G06V 2201/03; G06V 40/103; G06V 10/82; A61B 2560/0487; A61B 5/00
USPC .......................................................... 382/128
See application file for complete search history.

(56) References Cited

U.S. PATENT DOCUMENTS

| | | | | |
|---|---|---|---|---|
| 2012/0025080 | A1* | 2/2012 | Liu | H04N 23/88 |
| | | | | 250/332 |
| 2013/0261470 | A1* | 10/2013 | Allison | A61B 5/7278 |
| | | | | 600/476 |
| 2015/0223730 | A1 | 8/2015 | Ferrantelli | |
| 2016/0253798 | A1* | 9/2016 | Barrett | G16Z 99/00 |
| | | | | 348/77 |
| 2018/0153959 | A1* | 6/2018 | Fetissov | A61K 38/164 |
| 2018/0289334 | A1* | 10/2018 | De Brouwer | G06N 5/046 |
| 2019/0198169 | A1* | 6/2019 | T | G06F 16/951 |
| 2020/0196940 | A1* | 6/2020 | Stein | A61B 5/486 |
| 2020/0345314 | A1 | 11/2020 | Fedewa et al. | |
| 2021/0065394 | A1 | 3/2021 | Barnes | |
| 2021/0287804 | A1* | 9/2021 | Barnes | G06T 7/0012 |
| 2021/0358633 | A1* | 11/2021 | Barnes | G16H 30/40 |
| 2022/0301723 | A1* | 9/2022 | Bosanac | G16H 30/40 |
| 2023/0066883 | A1* | 3/2023 | Bosanac | G06T 7/0014 |

FOREIGN PATENT DOCUMENTS

| | | |
|---|---|---|
| GB | 2572425 A | 10/2019 |
| WO | 2012079014 A2 | 6/2012 |
| WO | 2014037939 A1 | 3/2014 |

* cited by examiner

100

PREDICTING USER BODY VOLUME TO MANAGE MEDICAL TREATMENT AND MEDICATION

CROSS REFERENCE TO RELATED APPLICATIONS

This application claims the benefit of U.S. Provisional Patent Application No. 63/170,910, filed 5 Apr. 2021, entitled "PREDICTING USER BODY VOLUME TO MANAGE MEDICAL TREATMENT AND MEDICATION," the disclosure of which is incorporated herein by reference in its entirety.

BACKGROUND

Medical treatment and medication are often recommended based on the patient's weight. For example, the medication dosage for an adult is different from that for a child. In certain medical treatment, such as cancer treatment, the treatment plan may be different for adults of different weights. However, in many existing medical treatments, a patient's weight does not directly establish a connection between the patient's body characteristics and the treatment plan, whereas the patient's body volume information, such as body volume index, body mass index, muscle mass, and body fat mass or volume, are not considered.

It is often not feasible to obtain body volume for a patient. For example, body scan technology, such as Dual-energy X-ray Absorptiometry (DXA, or DEXA), facilitates body composition measurement, but has disadvantages of being expensive, and time consuming. Furthermore, DEXA may have associated health implications. In this regard, whilst the amount of radiation used in the technology is typically extremely small, for repeated clinical and commercial use there have been recommendations that an individual should only be scanned twice per annum.

Medical treatment, such as cancer treatment, may have an impact on a patient's weight or body fat (e.g., muscle loss). Very often, this impact is not considered in medical treatment and medication control. Therefore, it may be desirable to estimate body volume information of a human body inexpensively, safely, and accurately.

In order to describe the manner in which the advantages and features of the present disclosure can be obtained, a description will be rendered by reference to specific examples, configurations, and embodiments of apparatus, methods, and systems which are illustrated in the appended drawings. Understanding that these drawings depict only typical embodiments of the present disclosure, and are not therefore to be considered to be limiting of its scope, the present disclosure will be described and explained with additional specificity and detail through the use of the accompanying drawings in which:

Figure 1:
FIG. 1 is a block diagram of a system for managing medical treatment and medication according to some examples described in the disclosure.
Figures 8A, 8B:
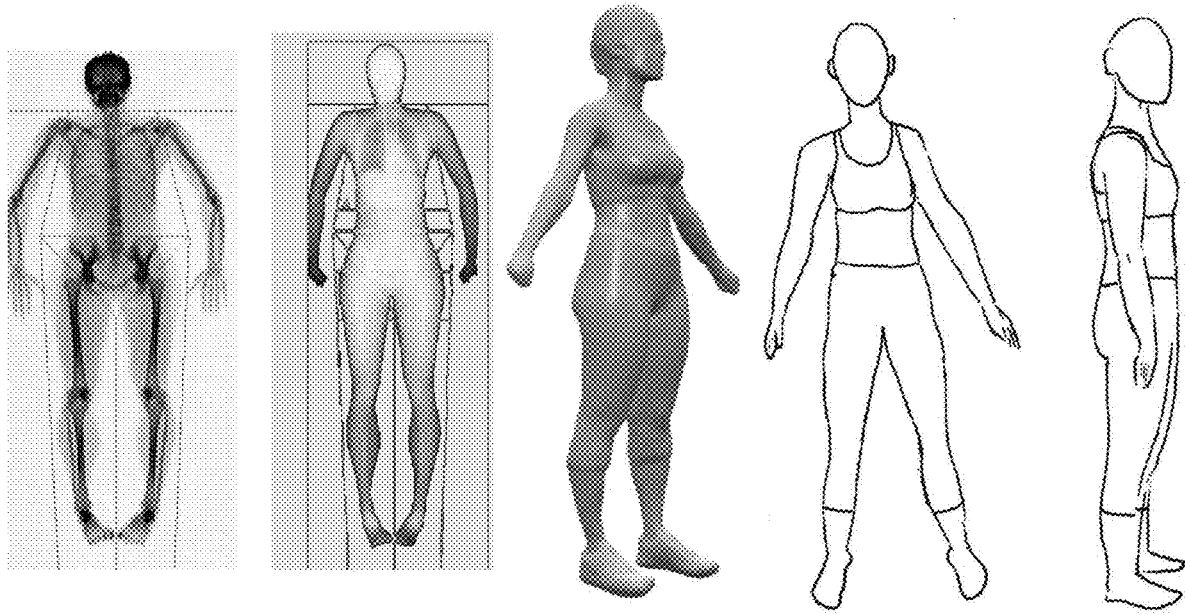
Figure 9:
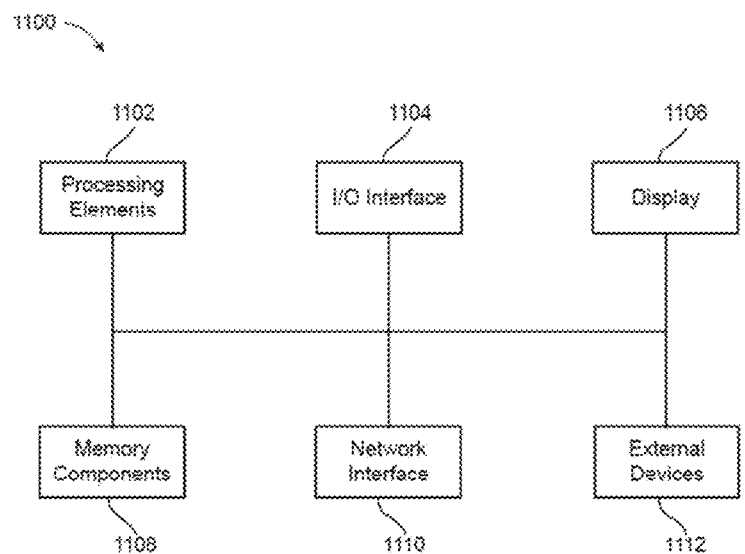

FIGS. 8A-8B illustrate examples of a computer generated person in 3D representation with specific shapes and body composition according to some examples described in the disclosure; and FIG. 9 is a block diagram of a computing device that may be used to implement with the system in FIG. 1 or integrated into one or more components of the system according to some examples described in the disclosure.

DETAILED DESCRIPTION

Certain details are set forth below to provide a sufficient understanding of examples of various embodiments of the disclosure. However, it is appreciated that examples described herein may be practiced without these particular details. Moreover, the particular examples of the present disclosure described herein should not be construed to limit the scope of the disclosure to these particular examples. In other instances, well-known circuits, control signals, timing protocols, and software operations have not been shown in detail in order to avoid unnecessarily obscuring embodiments of the disclosure. Additionally, terms such as "couples" and "coupled" mean that two components may be directly or indirectly electrically coupled. Indirectly coupled may imply that two components are coupled through one or more intermediate components.

Apparatus, methods, and systems disclosed herein solve a number of problems in the prior art noted above. That is, aspects of the present disclosure provide an easy, quick, safe, inexpensive, and completely non-invasive determination of a patient's body volume information. This information can be gathered and relayed frequently to a medical provider, such as a doctor or nurse, for formulating an optimal medical treatment plan. As the body volume characteristics of the patient change before or during treatment, such a treatment plan can be changed and tailored to meet the needs of the patient as time goes on. Treatment plans may include one or more of any number of medical interventions, including medications, diets, physical therapy, or the like. In particular, as used herein as a non-limiting example, aspects of the present disclosure include treatment plans for cancer, such as chemo-therapy and radiation dosages and schedules. The details of these apparatus, methods, and systems, as well as their advantages, are disclosed in more detail below.

FIG. 1 is a block diagram of a system 100 for managing medical treatment and medication according to some examples described in the present disclosure. In at least one example, the system 100 may include a body volume assessment system or device 104 and a medical treatment and/or medication management system or device 106. In some examples, system 100 may also include an image capturing device (not shown in FIG. 1). The image capturing device may be any device that can capture one or more images of the patient. Such images may be captured within the visible spectrum of light, for example using electromagnetic waves between about 400 nanometers and about 700 nanometers. The image capturing device may be, for example, a digital camera on a user's mobile phone, tablet, or other computing device. The image capturing device may also include a stand-alone camera, such as a digital camera. The "user," as referred to herein, may be any number of persons, including the patient, the patient's medical provider, or other person assisting the patient in obtaining the image or using the systems described herein.

The body volume assessment system or device 104, shown in FIG. 1, may be configured to extract body volume information about the user from at least one image capture by the image capturing device noted above. Once obtained, the medical treatment and/or medication management system or device 106 can receive that body volume information and develop and recommend a treatment plan for the patient. Details of each device/system 104, 106 shown in FIG. 1 are given in greater detail below. Such details describe the automatic features of each system 104, 106 that reduce the steps, time, and equipment necessary to perform the advantageous assessment of a patient's body volume and corresponding treatment plan generation. System 100 may be configured such that the patient (or other user) need only take a photograph using a widely available, personal image capturing device, such as their own mobile phone camera, in order to inform the patient's medical provider regarding a best course of medical treatment or changes to existing treatments that may be necessary.

Accordingly, the present disclosure details a method of determining treatment for a patient. Such a method is illustrated in at least FIGS. 1-4 of the present disclosure. A first step of the method may include obtaining an image of the patient. This step is illustrated at least in FIG. 4. The image may be captured by the patient himself/herself. The image may be a photograph, such as a digital photograph, of the exterior of the patient's body, including images generated from the visual spectrum of light, as noted above. For example, a patient or other user can capture the image of the patient's body in their own home using their own, day-to-day-use camera.

Another step of the method may include providing a recommendation for treating the patient based on information extracted from the image. The types of information, and how a recommendation may be generated therefrom, is described in greater detail below. This step of the method is illustrated at least in FIGS. 1-4. From the patient's or other users' points of view, as well as from the point of view of a medical provider, the above two steps may be the only steps necessary to take. In at least one example, all other intermediary steps, analysis, and data generation that enable the advantages described above may be performed automatically by the systems 104, 106 and devices described herein.

The body volume assessment system 104 may be configured to estimate, predict, or determine information about a patient's body volume, such as body mass, muscle mass, body fat, bone mineral density, or other body volume characteristics and information. In some examples, the body volume assessment system 104 may be coupled to an image capture device, e.g., a camera, to capture user images from different angles, and estimate the user's body volume information based on the user images. In some examples, the body volume assessment system 104 may use a machine learning network to predict the user body volume information from user images. The details of the body volume assessment system 104 will be further explained with reference to FIG. 2.

The body volume assessment system 104 may use a multivariate-based machine learning approach to build a 3D model of the patient from one or more captured images of the patient. Correlating certain visual characteristics of the patient from the image, such as the silhouette and joint positions of the patient (among other characteristics), system 104 can construct the 3D model from one or more machine learning training databases that include subjects having a similar age, gender, ethnicity, weight, height, and so forth. Once the 3D model of the patient is constructed, analysis can be performed by system 104, using the same or additional databases, to determine the various body volume characteristics found in the patient by learning (via machine learning algorithms) from known data of subjects in the training databases.

With continued reference to FIG. 1, system 100 may further include a medical treatment and medication management system 106 coupled to the body volume assessment system 104 via any suitable communication links. For example, the communication link may be wired, e.g., through Ethernet or cables. The communication link may also be wireless, e.g., Wi-Fi, 5G network, mesh network, Femtocell network, or other communication networks or a combination thereof.

The medical treatment and medication management system 106 may be configured to receive the body volume assessment data from the body volume assessment system 104, and use the body volume information in managing the medical treatment and medication. For example, the body volume may indicate the patient's body fat, muscle mass, total volume, body mass, bone mineral density, or other human body characteristics. The medical treatment system 106 may recommend adjustment of the medication dosage for the doctor based on the patient's body fat mass or volume. Such recommendation may be performed periodically, e.g., daily, weekly, monthly, or any other suitable period. For example, on a weekly basis, the body volume assessment system 104 may capture the patient's user images (e.g., via a mobile phone), and use the captured images to estimate, determine, or predict the various pieces of information about the patient's body volume noted above. The medical treatment and medication management system 106 may provide a recommendation for adjusting of the medication dosage or medical treatment plan. Then, the doctor may evaluate the recommendation by the medical treatment and medication management system 106 and decide on proper adjustments (or no adjustments) of the treatment and medication plan for the patient accordingly.

For example, if a patient's body fat percentage or volume increases, as indicated by the body volume assessment system 104, the medical treatment and medication management system 106 may provide a recommendation to increase a dosage or type of medication. Likewise, for example, if a patient's body fat percentage or volume decreases, as indicated by the body volume assessment system 104, the medical treatment and medication management system 106 may provide a recommendation to decrease a dosage or type of medication. The recommendation provided by the medication dosage or medical treatment plan 106 may depend on any of the body volume information gathered by the body volume assessment system 104.

Advantageously, in this way, as a patient's body changes, either due to aging, health, or any other event that affects the body composition of the patient, system 100 can assist the doctor (and/or patient) in providing the most effective medication dosage and treatment.

Additionally, or alternatively, in at least one embodiment of system 100, the body volume assessment system 104 may determine the location and/or distribution of body composition components, such as fat and muscle, and then the medication dosage or medical treatment plan 106 can make recommendations accordingly. For example, in at least one embodiment, body volume assessment system 104 is configured to identify excess abdominal fat. Once communicated, the medication dosage or medical treatment plan 106 may recommend variations to a radiation therapy directed towards abdominal organs. The same may be applied to breast cancer treatments as the fat composition of a patient's breast changes before or during treatment.

Figure 2:
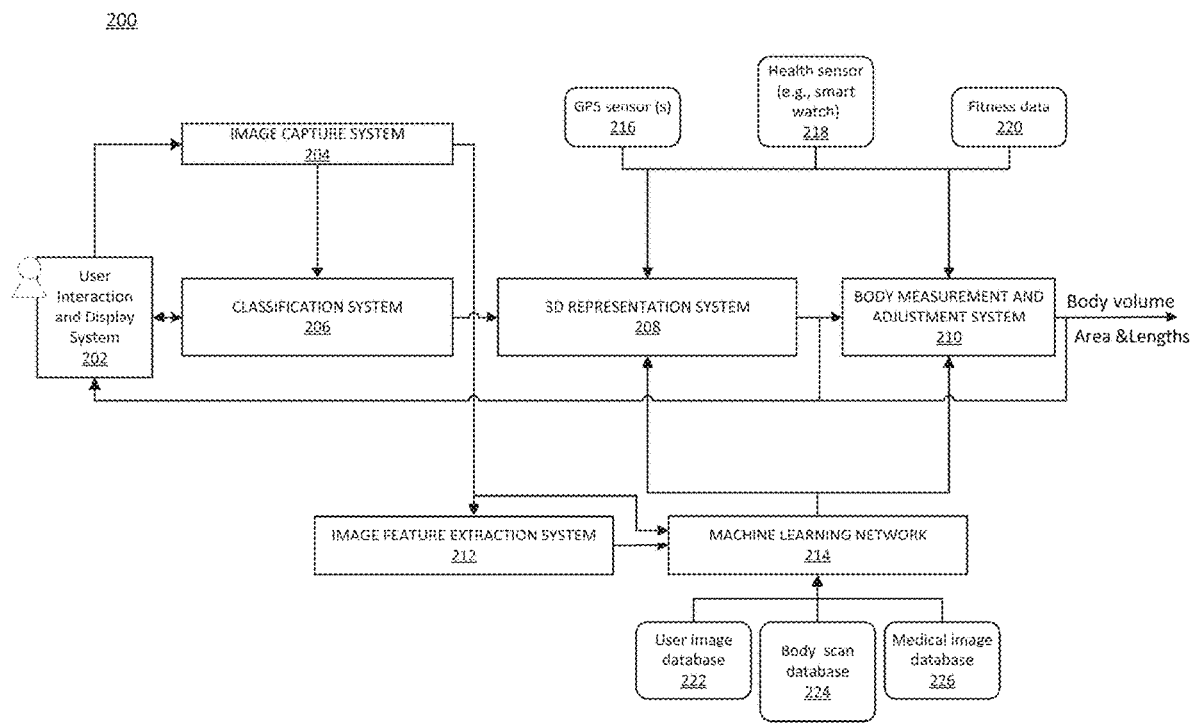
FIG. 2 is a block diagram of a system for predicting body volume of a human body according to some examples described in the disclosure.

FIG. 2 is a block diagram of a system 200 for predicting body volume information of a human body according to some examples described in the disclosure. In some examples, system 200 may be implemented in the body volume assessment system 104 (FIG. 1). In some examples, system 200 may include an image capture system 204 that includes an image capture device, such as a camera (e.g., a mobile phone with built-in camera or a stationary camera). The image capture device may be configured to capture one or more photographic images of a user from multiple views.

The system 200 may include a user interaction and display system 202 coupled to the image capture system 204. The user interaction and display system 202 may include a computer display configured to provide visual and audio aids to guide the user to capture optimal images depending on whether the user is capturing the images by herself/himself or another person is capturing the images. For example, during the capturing of user images, the user interaction and display system 202 may display a visual representation of a human body, such as skeleton or silhouette, to guide the user to move a part of the body to a desired position so that the captured body image aligns with the representation.

In some examples, the representation may include a human body contour, a bounding box, or other symbols to indicate a suggested position of one or more body parts or a whole body of the user. For example, system 202 may display a representation of arms to guide the user to move the arms or stretch the arms in a desired posture. Similarly, system 202 may display a representation of an entire body, which may include the head, the arms, the legs, the chest, and/or other parts of the body. The representation may be generated based on a first captured user image from the image capture system, such that the representation is displayed on the display of the user interaction and display system 202 in proportion to the images being captured.

In some examples, the system 200 may include a 3D representation system 208 configured to receive the user images captured from the image capture system 204 and use the user images to generate 3D representations of the human body. In some examples, the 3D representation system 208 may use a machine learning network 214 to predict the 3D representations of the human body based on the user images. The machine learning network 214 may be configured to train a machine learning model based on one or more databases of various types. For example, the machine learning model may be trained from previously captured user images stored in a user image database 222. Additionally and/or alternatively, the machine learning model may also be trained based on body scan parameters in a body scan database 224. In some examples, the body scan parameters may be collected from DEXA scans for various parts of a human body. For example, the body scan parameters may include body fat and/or bone mineral density (measured in Z-score and T-score) for different parts of a body, such as the torso, the thigh, or the waist etc. Additionally, and/or alternatively, the machine learning model may also be trained based on medical images stored in a medical image database 226. In some examples, the medical images may include medical images captured from medical imaging devices, such as a CT or an MRI. In some examples, the medical images may include anatomical landmarks. In a non-limiting example, examples of anatomical landmarks may include certain parts of a body, such as a mid-tummy point (belly button), or one or more joints of a body. The use of various types of databases, such as the user image database 222, the body scan database 224, the medical image database 226, may provide a more accurate prediction of 3D representations of a human body by incorporating various features of the human body. The details of the machine learning network 214 are further described in the present disclosure.

With further reference to FIG. 2, the system 200 may further include a body measurement and adjustment system 210. In some examples, the system 210 may receive the predicted 3D representations of a human body provided by the 3D representation system 208 and further fine-tune the 3D representations. Additionally, the system 210 may also generate or determine body volume information of an individual based on the 3D representations. As disclosed with reference to FIG. 1, the body volume may indicate the patient's body fat, body mass, muscle mass, water content, bone mineral density, or other human body characteristics. As with the 3D representation system 208, the body measurement and adjustment system 210 may also use the machine learning network 214, the details of which are further described in the present disclosure.

In some examples, one or more of the 3D representation system 208 and body measurement and adjustment system 210 may receive data from various sensors and/or databases. For example, a GPS sensor 216 may be configured to provide a user geographical location. A health sensor 218 may be configured to provide user health data, such as the heart rate, the pulse of a user. In some examples, the health sensor 218 may be a smart watch that provides the above health data. The health sensor 218 may also include a MEM sensor configured to provide acceleration associated with user movement. This data may indicate the user's activeness. Additionally, and/or alternatively, user fitness data, which indicates the activeness of a user, may be used to build the 3D representation of the human body.

Additionally, and/or alternatively, the body measurement and adjustment system 210 may receive user medical treatment data and use the medical treatment data to adjust the body measurement. For example, when the user is going under cancer treatment, the user's body fat may change. When the user is taking medication, the user's body fat may also change depending on the medication dosage, the period the user has been taking the medication, the user's diet, the user's age and gender etc. In some examples, the medical treatment data may include the type and period of the treatment, the name of the medication, the dosage and the time period in which the medication is being taken, the user's diet, age, gender. These various medical treatment data may be used in various combinations to adjust the body measurement. Additionally, the medical treatment data may also be used in combination with user activeness data during the medical treatment. For example, a user under cancer treatment without doing any exercise (or inactive) may tend to lose muscles or gain body fat.

With further reference to FIG. 2, the system 200 may include an image feature extraction system 212 coupled to the machine learning network 214. The image feature extraction system 212 may be configured to extract various features from the captured images to be used by the machine learning network 214.

Additionally, and/or alternatively, the system 200 may include a classification system 206 coupled to the 3D representation system 208 or body measurement and adjustment system 210. In some examples, the classification system 206 may be configured to score the images captured from the image capture system 204 to determine the acceptability of images for the machine learning network 214. In some examples, the classification system 206 may include a machine learning system configured to analyze the captured images (e.g., from image capture system 204) and score the images, where the scores indicate an acceptability. For example, a score may indicate if the background of an image is good, how good/bad the user's position, pose or orientation is with respect to the expected one.

Further details of the system 200 are provided below.

Classification System

In some examples, the classification system 206 may be configured to cluster the captured user images from 204 and segment the foreground and background of the images. In a non-limiting example, the system 206 may perform facial recognition on the user images to identify the face of the user, then use the face as a seed region for the foreground. In some examples, based on the segmentation result, the system may generate a skeleton and display the skeleton on the display of the user interaction and display system 202, to guide the user with capturing of additional images. The skeleton may be based on the segmented foreground region. In other examples, the system may prompt the user (e.g., via the user interaction and display system 202) to enter the user's height and weight, and use the user's height and weight to construct a skeleton from a pre-stored database. Additional data, such as gender, age etc. may be used to construct the skeleton.

In some examples, the classification system 206 may use a 2D joint model and generate a contour based on the 2D joint model.

In some examples, the classification 206 may analyze the captured user images and score them to determine if the images are acceptable to subsequent machine learning process, such as the machine learning network 214 to be used for 3D representation system 108 or body measurement and adjustment system 210.

Machine Learning Network and 3D Representation System

With further reference to FIG. 2, the machine learning network 214 may include a training system to train and optimize one or more machine learning models based on training data. The training data may be obtained from a user image database 222, a body scan database 224, and/or a medical image database 226. The trained machine learning models may be provided to the 3D representation system 208 to predict the 3D representations of the human body based on the user images. The details of the machine learning network 214 and 3D representation system 208 are further described with reference to FIG. 3.

Figure 3:
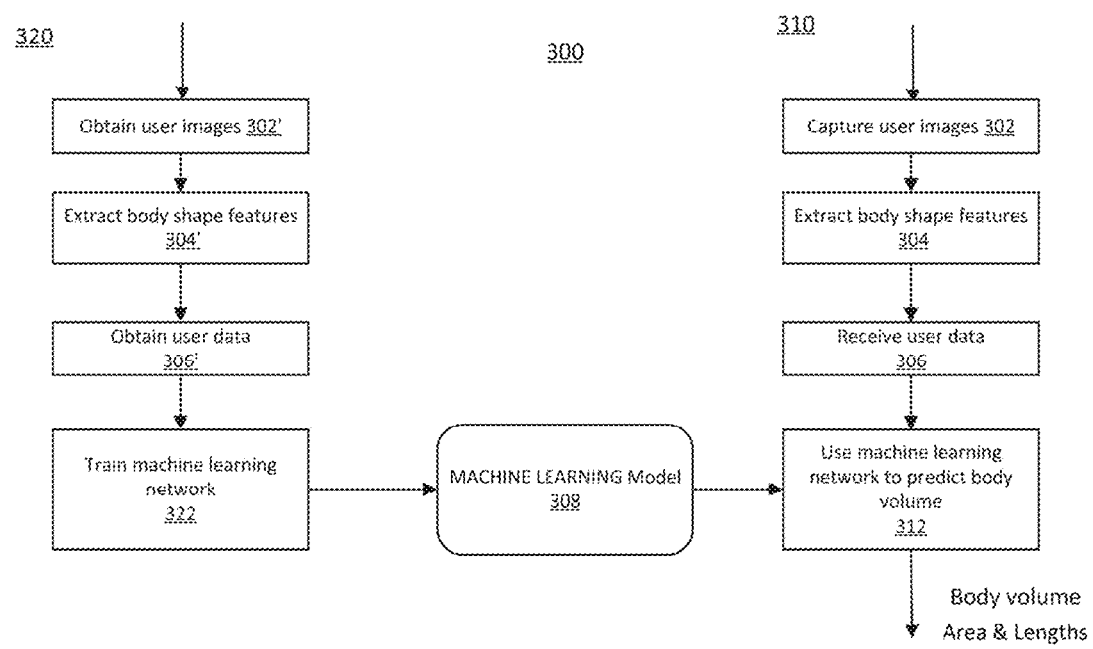
FIG. 3 is an example process for predicting a person's body volume using a machine learning network according to some examples described in the disclosure.

FIG. 3 is an example process for predicting a person's body volume using a machine learning network according to some examples described in the disclosure. In some examples, the process 300 may be implemented in the body volume assessment system 104 (FIG. 1) or the 3D representation system 208 (FIG. 2). With reference to FIG. 3, the process 300 may include a prediction process 310. The prediction process 310 may include capturing user images at operation 302. For example, the operation 302 may be performed in the image capture system 204 (FIG. 2) to obtain one or more user images, such as a front image, side image, back image, and/or user images from different angles. The user images may be facial images, upper body images, and/or whole body images.

In some examples, process 310 may further include extracting body shape features at operation 304. In some examples, the operation 304 may be implemented in the image feature extraction system 212 (FIG. 2). Examples of the body shape features may include 2D silhouettes representing the foreground of a human body, 2D joints or other body shape features. In some examples, the body shape features may be obtained based on the captured user images. Additionally, and/or alternatively, process 310 may further include receiving user data at operation 306. For example, the operation 306 may receive user entered data, e.g., user's weight, height, age, gender, ethnic group etc. This operation may be implemented in the user interaction and display system 202 (FIG. 2), in some examples. Operation 306 may further assess one or more databases to retrieve other user data, such as user health fitness data.

With continued reference to FIG. 3, process 310 may further include using a machine learning network to determine, estimate, or predict body volume information at operation 312, based on the extracted body shape features (304) and/or received user data (306). Operation 312 may be implemented in the 3D representation system (208 in FIG. 2) or the body volume assessment (104 in FIG. 1), in some examples. As discussed with respect to embodiments in FIGS. 1 and 2, the predicted body volume information may include body fat volumes or percentages, body mass index, bone mineral density or other human compositional characteristics. The body volume information may be predicted using the machine learning model 308. The machine learning model may include a body volume model. In some examples, the machine learning may also include a 3D body shape model. The body volume and 3D body shape model may be trained. Details of training the model are further described.

Now, with further reference to FIG. 3, the process 300 may include a training process 320 for training the machine learning model 308. In some examples, the process 320 may include obtaining the user images at operation 302', extracting body shape features at operation 304', and obtaining user data at operation 306'. The process 320 may use the images/features/data from the operations 302', 304', and/or 306', to train the machine learning model at operation 322. The processes 302', 304', and 306' may be performed in the same manner as processes 302, 304 and 306, respectively, except that the user images obtained from operation 302' are different from the user images captured from operation 302, and that the user data obtained from 306' are different from those obtained from 306.

In non-limiting examples, the operation 302' may retrieve user images from a training data set. For example, the training data set may contain a collection of training user images and/or training user data previously captured or collected, along with ground truth data associated with the training data set. The ground truth data may contain the ground truth 3D body shape and/or other body features, such as body volume information.

In some examples, the training data may include multiple and/or multivariate sets each collected from a subject in a group of subjects, and each set containing a corresponding ground truth data set. In some examples, the operation 322 may train the machine learning network to generate a machine learning model 308 based on the collected training data. In some examples, the training process 322 may generate a single machine learning model 308 based on the collected training data from the group of subjects.

In some other examples, the training process 322 may generate multiple machine learning models 308, each based on the training data from a sub-group of subjects or a single subject. For example, the training process may generate a machine learning model for a sub-group of the training subjects divided by ethnic group, by gender, by age, by height, or by other demographical measures, such as profession, education etc. The machine learning model 308 may thus include one or more models (e.g., 308 in FIG. 3).

Returning to process 310, the user images and user data (e.g., weight, height, age, etc.) may be obtained in real-time from the user via the image capture system 204 and/or user interaction and display system 202. The user data may also be obtained from one or more sensors or databases (e.g., user fitness data) as previously described. The operation of predicting the body volume may be performed using the machine learning model 308 learned from the process 320.

In some examples, a 3D shape model may comprise a plurality of 3D shape parameters. Examples of 3D shape parameters may include height, weight, chest circumferential measurement, etc. or additional parameters associates with a human body shape. In a non-limiting example, the 3D shape parameters may include 15 parameters. Other suitable number of body shape parameters may also be possible.

In some examples, the machine learning training process 320 may be configured to train a 2D joint model of a human body from user images, e.g., those captured from the image capture system 204. The 2-D joint model may include multiple joints of a human body in 2D domain and may be used by the training operation 322. For example, operation 322 may use the information from the 2D joint model to obtain the 3D body shape model of the human body. The machine learning network may also use other information, such as user's age, weight, gender, ethnic group, etc., which may be entered by the user via the user interaction and display system 202. In some examples, a 2D joint model may include a plurality of parameters representing skeletal joint positions. As such, training the 2D joint model includes training the parameters of the 2D joint model. An example of 2D joint positions is further illustrated in FIGS. 5A-5C.

Figures 5A, 5B, 5C:
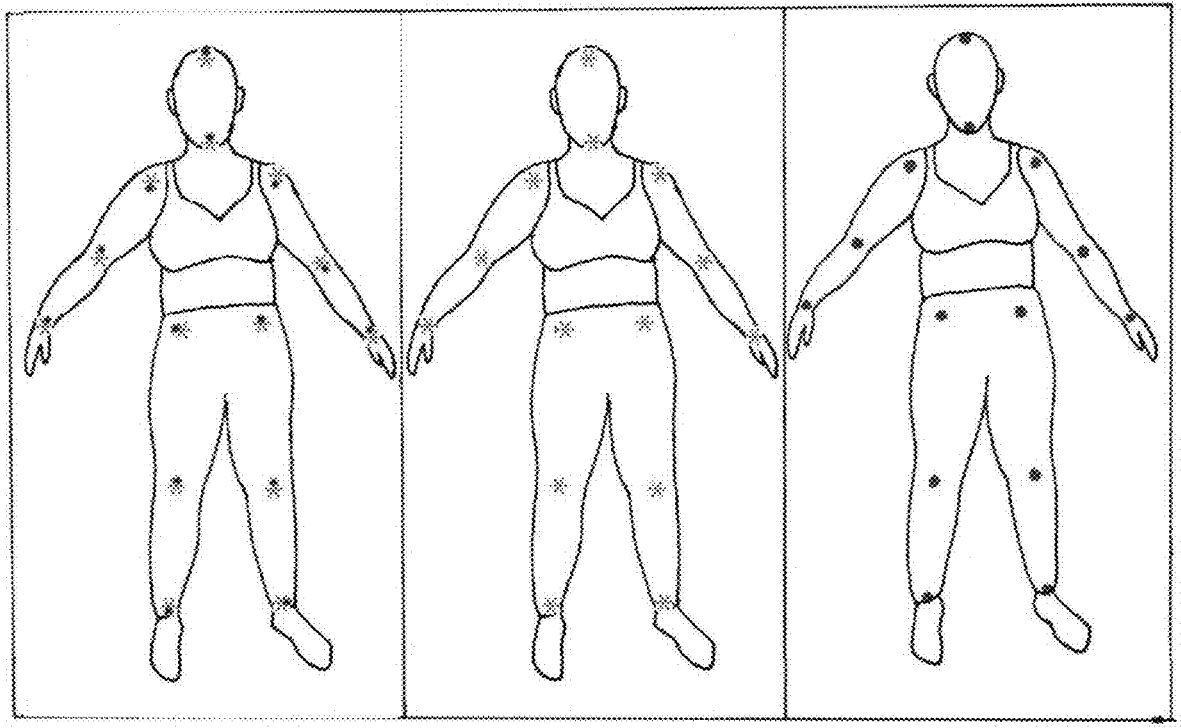
FIGS. 5A-5C illustrate examples of background segmentation and joints estimation according to some examples described in the disclosure.

FIGS. 5A-5C illustrate examples of background segmentation and joints estimation according to some examples described in the disclosure. For example, FIG. 5A shows an example user image from the image capture system (e.g., 204 in FIG. 2). FIG. 5B shows the segmentation result on the captured user image in FIG. 5A, where the foreground is separated from the background. FIG. 5B includes multiple skeleton joint points (shown in red) of the user's body shown in the user image, such as the chin, shoulder points, elbows, wrists, waist, knees, and ankles, as identified visually from the image. FIG. 5C shows corresponding estimated skeleton joint points (in green) overlaid on the same image, where the estimated multiple skeleton joint points are obtained from the machine learning network 214 (in FIG. 2) or machine learning model (308 in FIG. 3).

The skeleton joint points shown in FIG. 5B and the skeleton joint points shown in FIG. 5C are overlaid on the original user image in FIG. 5A. As shown, the skeleton joint points from the machine learning network (in green) align closely with the skeletal join points. In some examples, the estimated joint points, as identified by the machine learning network 214 (in FIG. 2) or machine learning model (308 in FIG. 3) may be more accurate at determining the actual positions of skeletal joint points than those identified by a human.

Figures 6A, 6B:
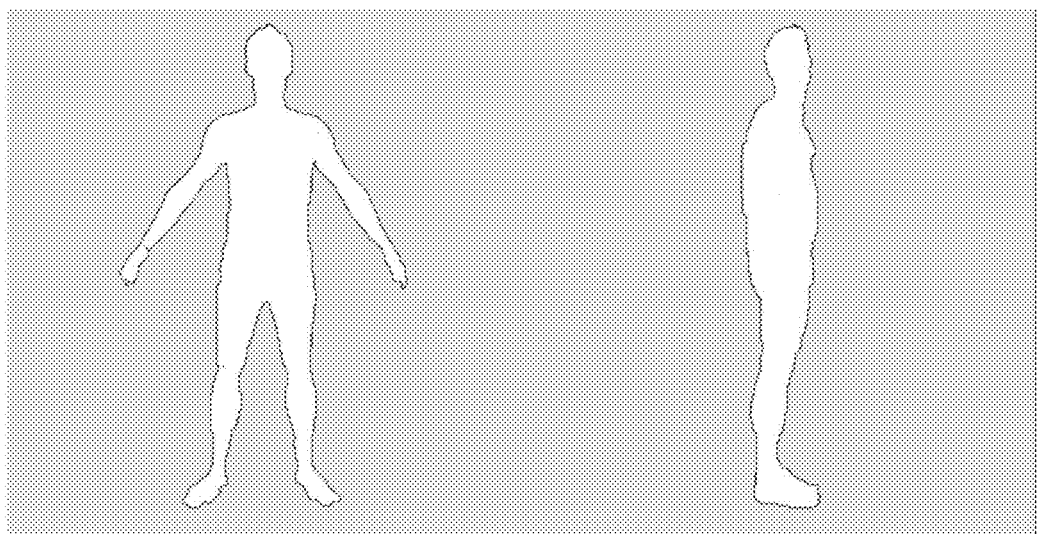
FIGS. 6A-6B illustrate examples of front and side views of a person according to some examples described in the disclosure.

In some examples, the system (e.g., 100 in FIG. 1, or 200 in FIG. 2) may receive captured user images (e.g., from the image capture system 204 in FIG. 2) and use the received images to estimate the body joints (in 2D domain) via the machine learning network 214. The system may obtain a contour of the human body from the trained 2D joint model by connecting the joints in the 2D joint model, followed by an image dilation. The contour defines the exterior boundary of the user's 2D representation. In FIGS. 6A and 6B, examples of front and side views of a person in 2D representation are shown, respectively.

Returning to FIG. 2, the machine learning network 214, which may implement the training process 320 (FIG. 3), may be configured to train user body volume. In some examples, the training data may be retrieved from body scan database 224. The machine learning network 214 may train a machine learning model to learn the weights and parameters that indicate body volume and use the trained machine learning model to predict a future human body volume from captured user images. In some examples, the training of the 3D body shape and body volume may be performed on an individual basis, which allows the system to be able to monitor/estimate an individual's body parameters over time.

Examples of the machine learning model used in the machine learning network 214 may include U-net, V-net, or other machine learning models. Additionally, and/or alternatively, the machine learning model may also include a suitable convolution neural network (CNN), such as VGG-16 or other CNNs. In some examples, the machine learning network 214 may perform the training in a training process (e.g., 320 in FIG. 3) by using the user images (e.g., 222) and the medical images (e.g., 226) together. This is further described below.

Returning to FIG. 1, in some examples, once the machine learning model is trained (learned), the system may use the learned model to estimate (or predict) the 3D body, 2D joint model, or the body volume, or a combination thereof from captured user images. In some examples, once the system (e.g., 100 in FIG. 1) has predicted the body volume from one or more captured user images, the system may compare the distribution of a patient's body volume over time to evaluate the effectiveness of medical treatment or medication. The system may further adjust the treatment or medication based on the evaluation result. For example, the medical treatment and medication management system 106 may determine that the patient has gained body fat during the treatment period, and in response, adjust the treatment plan or medication dosage.

Returning to FIG. 2, the 3D representation system 208 may incorporate various features in using the machine learning network 214. In some examples, the 3D representation system 208 may incorporate user locations (e.g., from GPS sensor) to estimate the user's ethnic group, and use a 3D or 2D body model specific to that particular ethnic group. In other words, the machine learning network 214 may train different models for different ethnic groups, each associated with a geographical location. In training a model for a given ethnic group, images of users in that ethnic group may also be used. In predicting the user's 3D body shape and body volume, the system may determine the user's ethnic group based on the user's location when the images are being captured, then use a corresponding model or training data associated with that ethnic group.

Image Feature Extraction System

With further reference to FIG. 2, in image feature extraction system 212, the image features to be extracted from captured images may include 3D shape parameters, depth information, user's micro movement, or curvature information. In some examples, the feature extraction system 212 may be configured to determine user's health information without using a health sensor. For example, the system may use pixel amplification to detect micro body movement (e.g., detecting micro movement in breathing from face images) to get health data, such as the heart rate, without using a health sensor.

Figure 7:
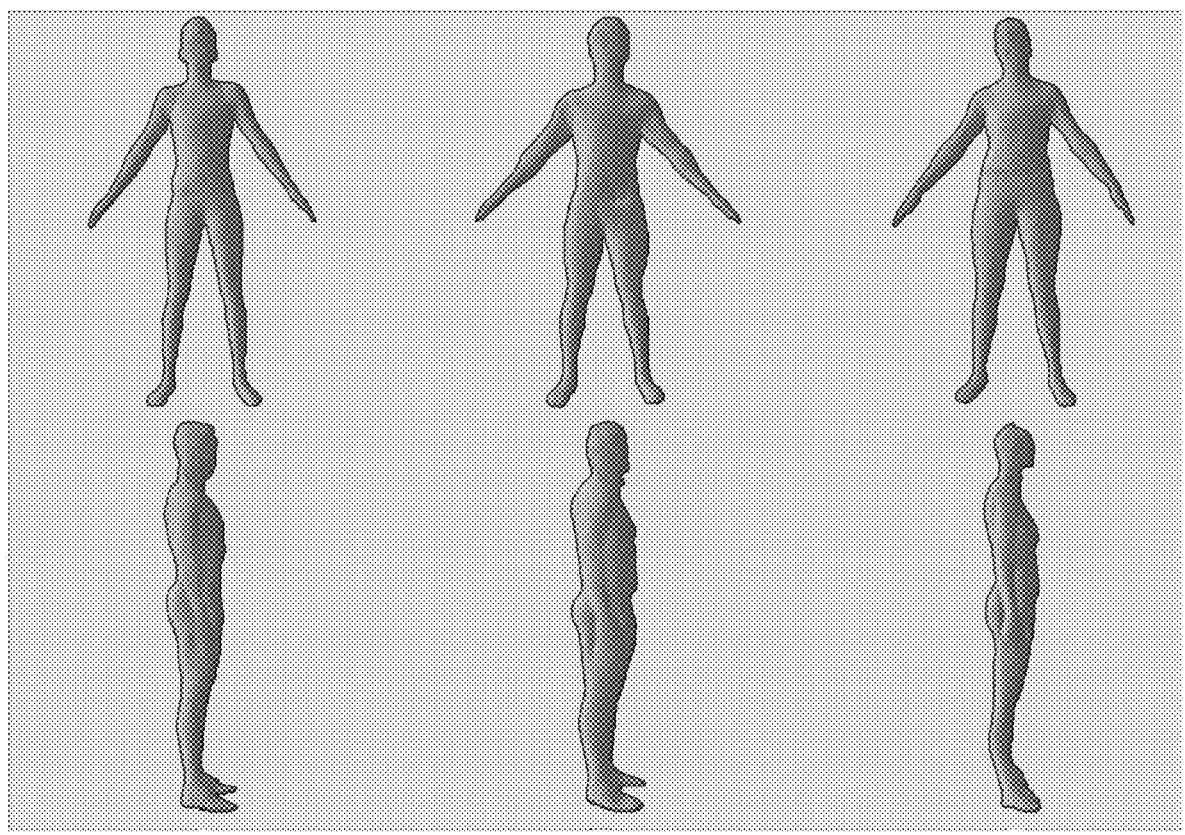
FIG. 7 illustrate various views of a constructed human body having UV depth-perceptive features extracted from photographic images according to some examples described in the disclosure.

In some examples, the image feature extraction system 212 may further be configured to extract UV depth-perceptive features from the captured images. The UV depth feature may include normals of surfaces of a person to give a perception of depth information. In some examples, the system may use a UV depth sensor to obtain depth information, such as vectors normal to the surfaces. In some examples, the depth sensor may be installed in a mobile phone or other mobile electronic device. The system may use the depth information to determine curvature of surfaces of the person's body. This information may be used by the machine learning network 214 to improve accuracy of the estimation. For example, the machine learning network 214 may determine the fat/muscle distribution based on the depth of the human body. FIG. 7 shows examples of estimated 3D body shape with depth information in various angles. Any number of depth-perceptive sensors can provide data to be incorporated into the present systems and methods to further improve the accuracy of the machine learning estimation. According to one example, the depth-perceptive sensors can include, but are in no way limited to, structural light sensors, time of flight sensors, or camera array sensors, or any combination thereof.

Body Measurement and Adjustment System

With further reference to FIG. 2, the body measurement and adjustment system 210 may be configured to adjust the body composition data or measurements. For example, if the user is athletically active (e.g., running or jogging on a regular basis, which information may be obtained from a health sensor or based on pixel-based image analysis on amplified body movement), the system may adjust the body composition to be on the "lean" side. For example, the system may obtain estimated body fat from the machine learning network 214 and increase the estimated body fat by a percentage. Conversely, if the user is less active, the system may adjust the body volume to decrease the estimated body fat by a percentage.

In some examples, the body measurement and adjustment system 210 may further be configured to determine whether a posture of a human body is acceptable to the machine learning network for accurate body measurement. The system may use trained 3D body shapes to make the determination. If the posture of the human body is not acceptable, the system may prompt the user (e.g., via user interaction and display system 202) to correct the posture, e.g., to stand still, to get the correct measurement. For example, a message may be displayed to the user on the capturing screen to prompt the user to stand still. Alternatively, and/or additionally, the system may display a skeleton to guide the user to ensure that the user's body in the capturing screen align with the skeleton. Furthermore, the system may detect a user positioning or posture that is not aligned with the preferred skeleton orientation for the machine learning network for accurate body measurement, and may re-orient the image to closely approximate the desired preferred skeleton orientation. According to one example, a detection of a joint or user body part outside of an expected area, or an asymmetrical orientation between sides of the captured image can be interpreted by the system as a user orientation in a non-preferred orientation, resulting in the system re-orienting the image to more closely approximate the desired preferred skeleton orientation.

FIGS. 8A-8B illustrate examples of computer-generated person in 3D representation with specific shapes and body volume according to some examples described in the disclosure. For example, one or more components in the system 200 (in FIG. 2) may be implemented to estimate 3D body shape and body volume of a person based on captured user images from different angles. In some examples, the estimated 3D body shape and body volume may be displayed in an avatar, which mimics the exact shape and profile of the person in different clothes.

Various embodiments in FIGS. 1-8, such as 100 in FIG. 1, may be implemented in a single computing system. For example, in FIG. 1, the body volume assessment system 104 and the medical treatment and medication management system 106 may be integrated into a single system, e.g., a server or a cloud system in a hospital that allows a doctor to capture user images of a patient and execute/adjust a medical treatment or medication dosage for the patient. Alternatively, the system 100 in FIG. 1 may be implemented in a telemedicine environment comprising a user device, e.g., a mobile phone, and a medical treatment/medication management system, which will be further described with reference to FIG. 4.

Figure 4:
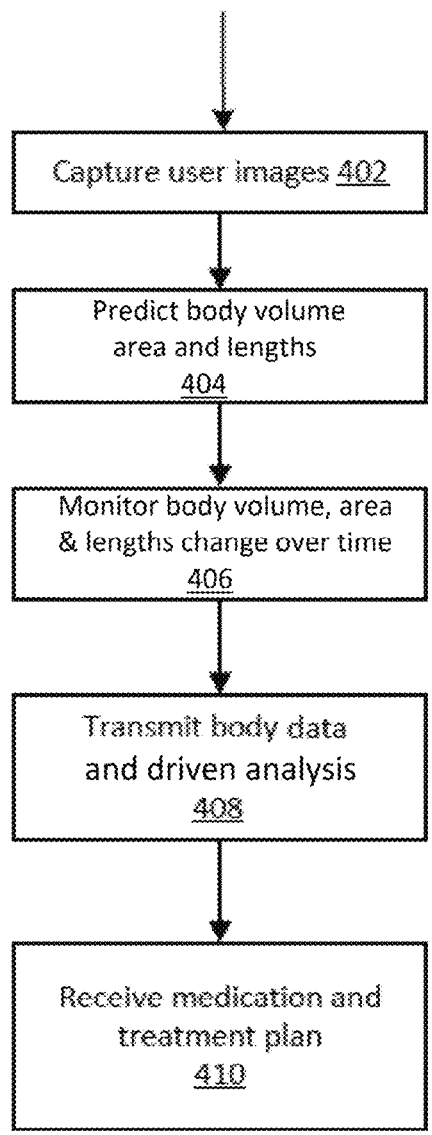
FIG. 4 illustrates example processes for managing medical treatment and medication plan in a telemedicine system according to some examples described in the disclosure.
Figure 4:
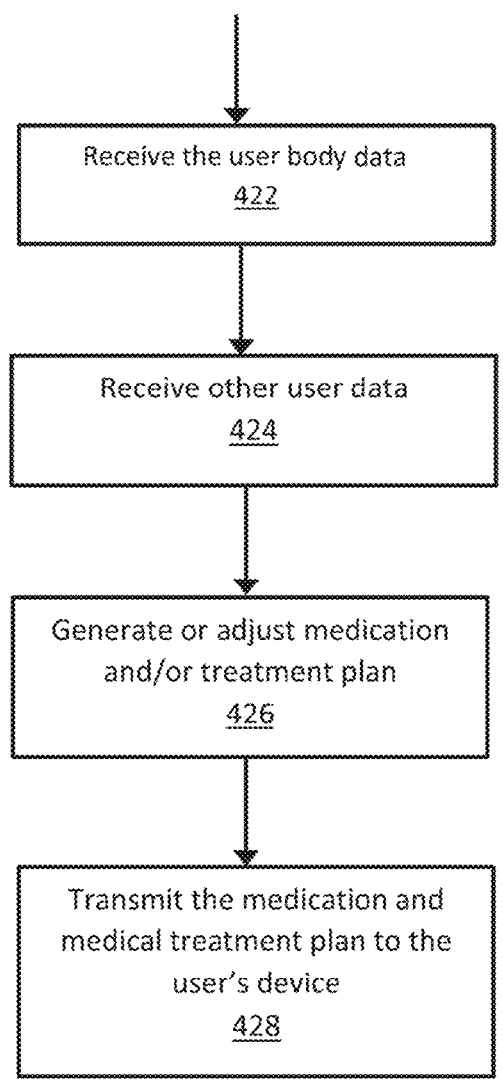

FIG. 4 illustrates example processes for managing medical treatment and medication plan in a telemedicine system according to some examples described in the disclosure. In a non-limiting example, a process 400 may be implemented in a user device, e.g., a mobile phone to predict the user's body volume in real time. For example, the process 400 may include capturing user images at operation 402. Optionally, the process 400 may also include a user interaction process to prompt the user to take multiple user images from different views. For example, operation 402 may be implemented by the user interaction and display system (202 in FIG. 2). The process 400 may also include predicting user body volume at operation 404. For example, the operation 404 may include one or more operations in the process 310 (FIG. 3). Alternatively, and/or additionally, the operation 404 may also implement one or more operations in the process 320 (FIG. 3).

Returning to FIG. 4, the process 400 may further include monitoring body volume changes over time at operation 406. For example, the body volume changes may include a difference of the predicted body volumes obtained from operation 404 at different times, e.g., a few days apart, a month apart, or a few months apart. The process 400 may transmit the predicted body volume at an instant time, and/or body volume changes to a medical treatment and medication management system at operation 408. In some examples, the medical treatment and medication management system may be implemented in the system 106 (FIG. 1). The process 400 may further receive medication and treatment plan from the medical treatment and medication management system at operation 410. For example, the received medication plan may include adjusted dosage for the medication prescribed to the patient. In response, the process 400 may further execute the adjusted medication, e.g., at operation 412. Executing the adjusted medication, e.g., dosage change or switch of medication, may include transmitting the medication information to a medication dispensing server in a pharmacy to dispense the medication to the patient.

With further reference to FIG. 4, a process 420 may be implemented in a medical treatment and medication management system, e.g., 106 in FIG. 1. The process 420 may include receiving the user body volume data at operation 422. For example, the user body volume data may be received from a user device. The user body volume data may include predicted user body volume or change of body volume over time, which may be obtained from process 400. Additionally, the process 420 may also receive other user data at operation 424. Other user data may include user's medical record, which may be retrieved from a medical record database. The process 420 may generate or adjust medication and/or treatment plan at operation 426, based on the user body volume data and/or other user data. For example, operation 426 may be implemented in the medical treatment and medication management system 106 (FIG. 1). In some examples, operation 426 may be intervened by a doctor to confirm, verify, or adjust the medical treatment or medication. The process 420 may transmit the medication and medical treatment plan to the user's device at operation 428. Alternatively, and/or additionally, operation 428 may include transmitting the medication to a dispensing server at a pharmacy. As described with respect to process 400, operation 410 may receive the transmitted medication and medical treatment plan.

FIG. 9 shows a simplified block structure for a computing device that may be used with the system 100 (in FIG. 1) or integrated into one or more components of the system. For example, the body volume assessment system 104, the medical treatment and medication management system 106, or one or more components of the systems 104, 106, such as the image capture system 204, the user interaction and display system 202, the classification system 206, the 3D representation system 208, the body measure and adjustment system 210, the image feature extraction system 212, or the machine learning network 214 may include one or more of the components shown in FIG. 9 and be used to implement one or more blocks or execute one or more of the components or operations disclosed in FIGS. 1-8. In FIG. 9, the computing device 1100 may include one or more processing elements 1102, an input/output interface 1104, a display 1106, one or more memory components 1108, a network interface 1110, and one or more external devices 1112. Each of the various components may be in communication with one another through one or more busses, wireless means, or the like.

The processing element 1102 may be any type of electronic device capable of processing, receiving, and/or transmitting instructions. For example, the processing element 1102 may be a central processing unit, microprocessor, processor, or microcontroller. Additionally, it should be noted that some components of the computer 1100 may be controlled by a first processor and other components may be controlled by a second processor, where the first and second processors may or may not be in communication with each other.

The memory components 1108 are used by the computer 1100 to store instructions for the processing element 1102, as well as store data, such as the knowledge base (e.g., 222, 224, 226 in FIG. 2), and the like. The memory components 1108 may be, for example, magneto-optical storage, read-only memory, random access memory, erasable programmable memory, flash memory, or a combination of one or more types of memory components.

The display 1106 provides audio and/or visual guidance to a user, such as displaying skeletons or other visual representations to guide the user in capturing one or more user images, or display other visual representation as may be implemented in the user interaction and display system 202 (FIG. 2). Optionally, the display 1106 may act as an input element to enable a user to control, manipulate, and calibrate various components of the computing device 1100. The display 1106 may be a liquid crystal display, plasma display, organic light-emitting diode display, and/or other suitable display. In embodiments where the display 1106 is used as an input, the display may include one or more touch or input sensors, such as capacitive touch sensors, resistive grid, or the like.

The I/O interface 1104 allows a user to enter data into the computer 1100, as well as provides an input/output for the computer 1100 to communicate with other devices or services (e.g., user interaction and display system 202 in FIG. 2). The I/O interface 1104 can include one or more input buttons, touch pads, and so on.

The network interface 1110 provides communication to and from the computer 1100 to other devices. For example, the network interface 1110 may implement the communication link 102 (FIG. 1) that allows various systems to communicate with each other. The network interface 1110 includes one or more communication protocols, such as, but not limited to WiFi, Ethernet, Bluetooth, and so on. The network interface 1110 may also include one or more hardwired components, such as a Universal Serial Bus (USB) cable, or the like. The configuration of the network interface 1110 depends on the types of communication desired and may be modified to communicate via WiFi, Bluetooth, and so on.

The external devices 1112 are one or more devices that can be used to provide various inputs to the computing device 1100, e.g., mouse, microphone, keyboard, trackpad, or the like. The external devices 1112 may be local or remote and may vary as desired. In some examples, the external devices 1112 may also include one or more additional sensors, such as sensor(s) 216, 218, 220 (in FIG. 2) that may be used in obtaining a user's body measurement.

The foregoing description has a broad application. For example, while examples disclosed herein may focus on central communication system, it should be appreciated that the concepts disclosed herein may equally apply to other systems, such as a distributed, central or decentralized system, or a cloud system. For example, the machine learning network 214, or other components (in FIG. 1) may be residing on a server in a client/server system. The machine learning network 114 may also reside on any device, e.g., a mobile phone, on the network and operate in a decentralized manner. The machine learning network 114, or a portion thereof may also be residing in a controller virtual machine (VM) or a hypervisor in a VM computing environment. Accordingly, the one or more components in the system 100 (FIG. 1) may be implemented in various configurations to achieve an optimal performance in terms of accuracy and processing speed. Thus, the disclosure is meant only to provide examples of various systems and methods and is not intended to suggest that the scope of the disclosure, including the claims, is limited to these examples.

The various embodiments described in FIGS. 1-9 provide advantages in predicting accurate body composition and thus body measurement based on user images captured from a mobile phone or other image capture devices, without requiring any expensive equipment at prescribed locations.

Each of the embodiments, examples, or configurations described in the detailed description above may include any of the features, options, and possibilities set out in the present disclosure, including those under the other independent embodiments, and may also include any combination of any of the features, options, and possibilities set out in the present disclosure and figures. Further examples consistent with the present teachings described herein are set out in the following numbered clauses:

Clause 1: An apparatus comprising: a processor; and computer readable medium containing programming instructions that, when executed, will cause the processor to: use a machine learning model and one or more images of a subject to predict body volume information; receive a medical treatment plan, wherein the medical treatment plan is based on the body volume information; and execute the received medical treatment plan.

Clause 2: The apparatus of clause 1, wherein the programming instructions, when executed, will further cause the processor to: transmit the predicted body volume information to a medication treatment and medication management system via a communication link; and receive the medication or medical treatment plan from the medication treatment and medication management system.

Clause 3: The apparatus of clause 1 or 2, wherein the machine learning model comprises a body volume model.

Clause 4: The apparatus of any of clauses 1-3, wherein the programming instructions, when executed, will further cause the processor to use a machine learning network to train the machine learning model based on at least on a training data set comprising a plurality of user images.

Clause 5: The apparatus of any of clauses 1-4, wherein the programming instructions, when executed, will further cause the processor to execute the received medical treatment plan by transmitting the medical treatment plan to a medication dispensing server.

Clause 6: An apparatus comprising: a processor; and computer readable medium containing programming instructions that, when executed, will cause the processor to: receive user body volume data from a user device via a communication link; adjust a medical treatment plan based on the received user body volume data; and transmit the adjusted medical treatment to the user device.

Clause 7: The apparatus of clause 6, wherein the programming instructions, when executed, will further cause the processor to: receive user data from the user device; and adjust the medical treatment plan based additionally on the received user body volume data.

Clause 8: The apparatus of claim 6 or clause 7, wherein the user body volume data includes a change of body volume over a period of time.

Clause 9: The apparatus of any of clauses 6-8, wherein the user body volume data comprises one or more of: body fat, body mass, or bone mineral density.

Clause 10: The apparatus of any of clauses 6-9, wherein the user body volume data comprises a distribution of body fat.

Clause 11: A method of determining treatment for a patient, comprising: obtaining an image of the patient; providing a recommendation for treating the patient based on information extracted from the image.

Clause 12: The method of clause 11, wherein the image comprises the exterior of the patient's body.

Clause 13: The method of clause 11 or 12, wherein the treatment comprises a medication dose or a change in a medication dose to be administered to the patient.

Clause 14: The method of clause 13, wherein a medication of the medication dose comprises a cancer medication.

Clause 15: The method of any of clauses 11-14, wherein obtaining the image comprises taking a photograph with an image capturing device.

Clause 16: The method of clause 15, wherein the patient takes the photograph.

Clause 17: The method of clause 15 or 15, wherein the photograph of the patient is taken in the visible light spectrum having an electromagnetic wavelength between about 400 nanometers and about 700 nanometers.

Clause 18: The method of clauses 11-17, wherein the information extracted from the image includes body volume information of the patient.

Clause 19: The method of any of clauses 11-18, wherein the information extracted from the image includes a body max index of the patient.

Clause 20: The method of any of clauses 11-19, wherein the information extracted from the image includes a body volume index of the patient.

Clause 21: A system for managing a treatment of a patient, comprising: an image capturing device that captures images in the visible spectrum; a body volume assessment device that extracts body volume information from at least one image captured by the image capturing device; and a medical treatment recommendation device that provides a treatment recommendation based on the body volume information extracted by the body volume assessment device.

Clause 22: The system of clause 21, the body volume assessment device comprising: a processor; and computer readable medium containing programming instructions that, when executed, will cause the processor to: use a machine learning model and one or more images captured by the image capturing device to predict the body volume information.

Clause 23: The system of clause 21 or 22, the medical treatment recommendation device comprising: a processor; and computer readable medium containing programming instructions that, when executed, will cause the processor to: receive the body volume information from the body volume assessment device; determine the treatment recommendation based on the body volume information extracted by the body volume assessment device; and provide the treatment recommendation to a treatment provider.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

From the foregoing it will be appreciated that, although specific embodiments of the disclosure have been described herein for purposes of illustration, various modifications may be made without deviating from the spirit and scope of the disclosure. Accordingly, the scope of the disclosure should not be limited any of the specific embodiments described herein.

What is claimed is:

1. An apparatus comprising:
   a processor; and
   computer readable medium containing programming instructions that, when executed, will cause the processor to:
      use a machine learning model and one or more images of a subject to predict body volume information;
      adjust the predicted body volume information based on at least one of user health data, medical treatment data, or analysis of the one or more images of the subject;
      receive a medical treatment plan, wherein the medical treatment plan is based on the adjusted body volume information; and
      execute the received medical treatment plan.

2. The apparatus of claim 1, wherein the programming instructions, when executed, will further cause the processor to:
   transmit the predicted body volume information to a medication treatment management system via a communication link; and
   receive the medical treatment plan from the medication treatment and medication management system.

3. The apparatus of claim 1, wherein the machine learning model comprises a body volume model.

4. The apparatus of claim 3, wherein the programming instructions, when executed, will further cause the processor to use a machine learning network to train the machine learning model based on at least on a training data set comprising a plurality of user images.

5. The apparatus of claim 1, wherein the programming instructions, when executed, will further cause the processor to execute the received medical treatment plan by transmitting the medical treatment plan to a medication dispensing server.

6. An apparatus comprising:
   a processor; and
   computer readable medium containing programming instructions that, when executed, will cause the processor to:
      receive user body volume data from a user device via a communication link;
      adjust the user body volume data based on at least one of user health data, medical treatment data, or analysis of one or more images of a subject of the user device;
      adjust a medical treatment plan based on the adjusted user body volume data; and
      transmit the adjusted medical treatment to the user device.

7. The apparatus of claim 6, wherein the programming instructions, when executed, will further cause the processor to:
   receive user data from the user device; and
   adjust the medical treatment plan based additionally on the received user body volume data.

8. The apparatus of claim 6, wherein the user body volume data includes a change of body volume over a period of time.

9. The apparatus of claim 6, wherein the user body volume data comprises one or more of: body fat, body mass, or bone mineral density.

10. The apparatus of claim 6, wherein the user body volume data comprises a distribution of body fat.

11. A method of determining treatment for a patient, comprising:
    obtaining an image of the patient;
    using a machine learning model and the image to predict body volume information;
    adjusting the predicted body volume information based on at least one of user health data, medical treatment data, or analysis of the image; and
    providing a recommendation for treating the patient based on the adjusted body volume information.

12. The method of claim 11, wherein the image comprises the exterior of the patient's body.

13. The method of claim 11, wherein the treatment comprises a medication dose or a change in a medication dose to be administered to the patient.

14. The method of claim 13, wherein a medication of the medication dose comprises a cancer medication.

15. The method of claim 11, wherein obtaining the image comprises taking a photograph with an image capturing device.

16. The method of claim 15, wherein the patient takes the photograph.

17. The method of claim 15, wherein the photograph of the patient is taken in the visible light spectrum having an electromagnetic wavelength between about 400 nanometers and about 700 nanometers.

18. The method of claim 11, wherein the information extracted from the image includes body volume information of the patient.

19. The method of claim 11, wherein the information extracted from the image includes a body max index of the patient.

20. The method of claim 11, wherein the information extracted from the image includes a body volume index of the patient.

21. A system for managing a treatment of a patient, comprising:
    an image capturing device that captures images in the visible spectrum;

a body volume assessment device that extracts body volume information from at least one image captured by the image capturing device;

an adjustment device that adjusts the extracted body volume information based on at least one of user health data, medical treatment data, or analysis of the at least one image;

a medical treatment recommendation device that provides a treatment recommendation based on the adjusted body volume information.

22. The system of claim 21, the body volume assessment device comprising:

a processor; and computer readable medium containing programming instructions that, when executed, will cause the processor to:

use a machine learning model and one or more images captured by the image capturing device to predict the body volume information.

23. The system of claim 21, the medical treatment recommendation device comprising:

a processor; and computer readable medium containing programming instructions that, when executed, will cause the processor to:

receive the body volume information from the body volume assessment device;

determine the treatment recommendation based on the body volume information extracted by the body volume assessment device; and provide the treatment recommendation to a treatment provider.

\* \* \* \* \*